United States Patent [19]

Nguyen

[11] Patent Number: 4,888,014
[45] Date of Patent: * Dec. 19, 1989

[54] ENDOCAPSULAR INTRAOCULAR LENS

[75] Inventor: Tuan A. Nguyen, Fountain Valley, Calif.

[73] Assignee: Allergan, Inc., Irvine, Calif.

[ * ] Notice: The portion of the term of this patent subsequent to Jun. 27, 2006 has been disclaimed.

[21] Appl. No.: 343,033

[22] Filed: Apr. 25, 1989

Related U.S. Application Data

[62] Division of Ser. No. 243,989, Sep. 13, 1988.

[51] Int. Cl.$^4$ .............................................. A61F 2/16
[52] U.S. Cl. ......................................................... 623/6
[58] Field of Search ............................................. 623/6

[56] References Cited

U.S. PATENT DOCUMENTS

| | | | |
|---|---|---|---|
| 4,122,556 | 10/1978 | Poler | 623/6 |
| 4,149,279 | 4/1979 | Poler | 623/6 |
| 4,249,271 | 2/1981 | Poler | 623/6 |
| 4,249,272 | 2/1981 | Poler | 623/6 |
| 4,251,887 | 2/1981 | Anis | 623/6 |
| 4,326,306 | 4/1982 | Poler | 623/6 |
| 4,363,143 | 12/1982 | Callahan | 623/6 |
| 4,377,329 | 3/1983 | Poler | 351/160 R |
| 4,418,431 | 12/1983 | Feaster | 623/6 |
| 4,439,873 | 4/1984 | Poler | 623/6 |
| 4,450,593 | 5/1984 | Poler | 623/6 |
| 4,477,931 | 10/1984 | Kelman | 623/6 |
| 4,494,254 | 1/1985 | Lopez | 623/6 |
| 4,581,033 | 4/1986 | Callahan | 623/6 |
| 4,666,445 | 5/1987 | Tillay | 623/6 |
| 4,681,586 | 7/1987 | Woods | 623/6 |
| 4,711,638 | 12/1987 | Lindstrom | 623/6 |

FOREIGN PATENT DOCUMENTS 8500527 1/1986 Netherlands ............................. 623/6

OTHER PUBLICATIONS

Randall Woods, DO, "A New Single-Haptic, One-Piece PMMA IOL", Jul. 15, 1987 issue of Ocular Surgery News.
Aziz Y. Anis, MD, "New Concepts In Circular Posterior Chamber Lenses", Oct. 1, 1987 issue of Ocular Surgery News.
"The Jaffe Single Piece Posterior Chamber Lens From Cilco", Advertisement Brochure-Cilco (2 pages) Oct. 1984, 623-626.

Primary Examiner—Ronald L. Frinks
Attorney, Agent, or Firm—Gordon L. Peterson; Loyal M. Hanson

[57] ABSTRACT

An intraocular lens includes an optic for implantation in a human eye and first and second fixation members attached to the optic for supporting the optic from the capsular bag of the eye, each of the fixation members having inner and outer legs. The inner legs extend radially outwardly and circumferentially from first and second attachment sites on the optic to intermediate portions of the fixation members. Each of the outer legs extend along an arc from the intermediate portion of the fixation member to a distal end portion of the fixation member. The arcs extend along a circle that is centered on an optical axis of the optic, the circle has a diameter that is approximately equal to the diameter of the capsular bag, and each of the first and second outer legs has a length such that the distal end portion of each of the fixation members is disposed proximate the intermediate portion of the other fixation member so that the first and second fixation members can abut a substantial portion of the capsular equator of the capsular bag and yet flex radially inwardly slightly to accommodate variations in the diameter of the capsular equator.

4 Claims, 1 Drawing Sheet

U.S. Patent    Dec. 19, 1989    4,888,014
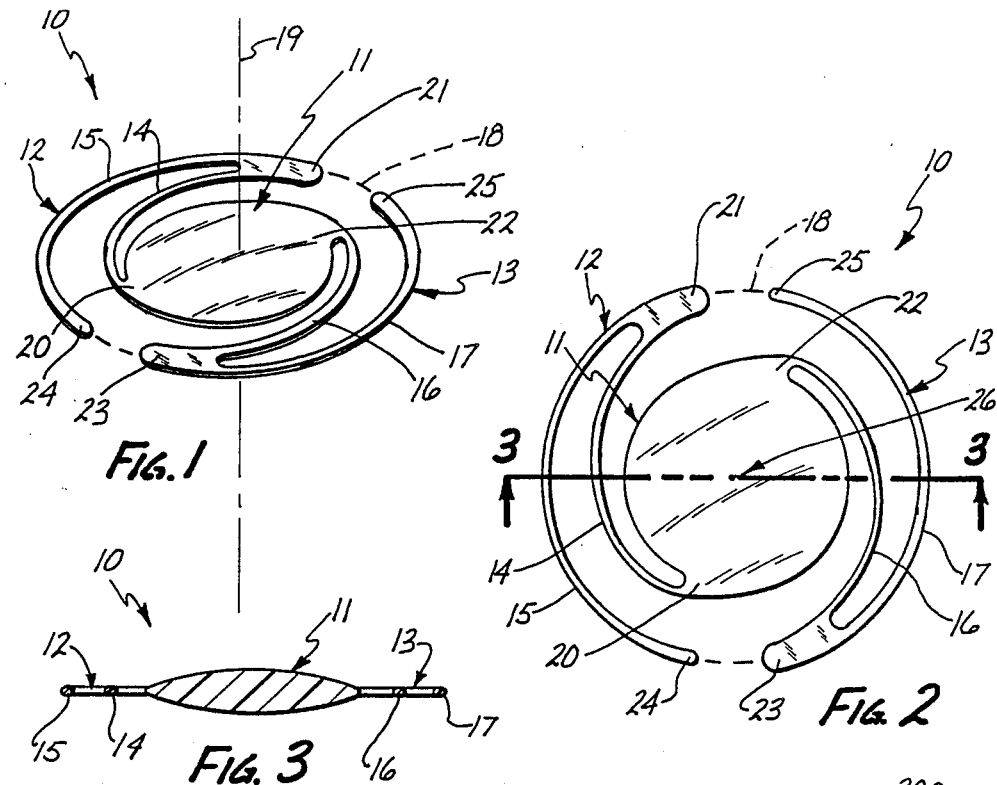
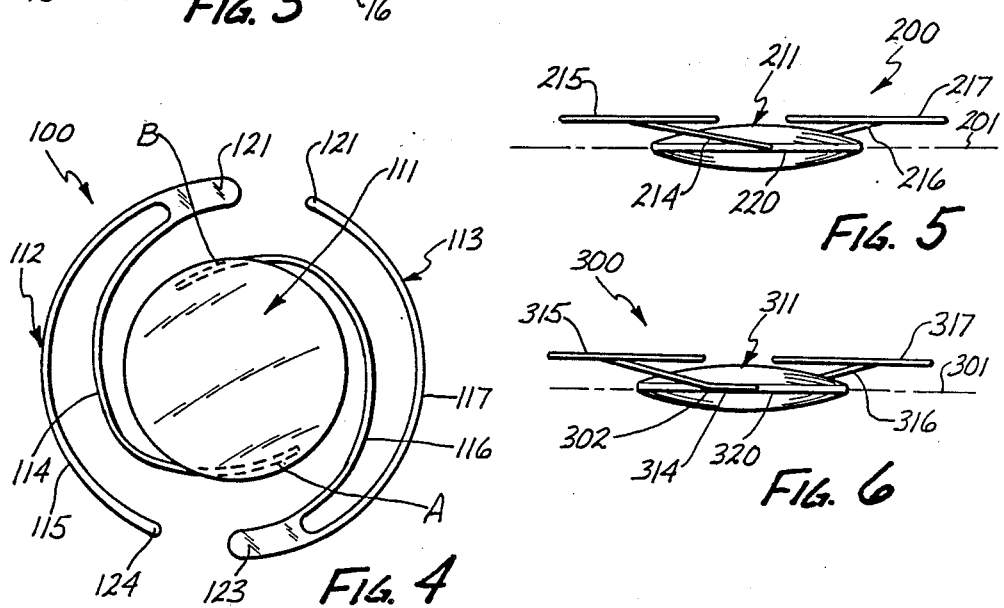

ENDOCAPSULAR INTRAOCULAR LENS

This application is a division, of application Ser. No. 243,989, filed 9/13/88.

BACKGROUND OF THE INVENTION

1. Technical Field

This invention relates generally to intraocular lenses, and more particularly to an intraocular lens designed for placement in the capsular bag of a human eye.

2. Background Information

Conventional intraocular lenses designed for use as circular posterior chamber lens may employ haptics or fixation members to support the optic from the capsular bag. The fixation members may take the form of independent flexible loops such as the common J-loop configuration, for example. However, these can result in uneven pressure being exerted on the capsular bag, decentration of the lens, and related problems.

Some improved lenses include one or more fixation members disposed in a circular configuration. Once the lens is introduced into the eye and placed in the capsular bag, the fixation members abut almost the entire capsular equator to provide more intimate contact. This inhibits lens decentration while achieving more consistent bag fixation and postoperative lens stability.

Four such lenses are illustrated in an article entitled "New Concepts In Circular Posterior Chamber Lenses" appearing in the Oct. 1, 1987 issue of *Ocular Surgery News*. The article reports an interview with Aziz Y. Anis, MD regarding his designs in which Dr. Anis explains that the circular configuration is the same outside the eye as inside the eye instead of having a spring action that results in the lens conforming to the capsular bag once it is put in the eye. Dr. Anis explains that this feature avoids an impaction along a chord or diameter of the circular capsule rather than simple contact with its entire circumference.

However, there are certain problems with the illustrated lens designs that need to be overcome. It is normal for the capsular bag to sometimes contract, for example, and nonconforming fixation members may tend to impair this action. Consequently, it is desirable to have a circular lens with fixation members that can better accommodate contraction of the capsular bag.

In addition, the bag is not always perfectly circular. As a result, a nondeformable, circular configuration might not maintain intimate contact with the bag equator as expected. Thus, it is desirable to have a circular lens with fixation members that can better accommodate a noncircular capsular bag also.

Furthermore, the size of the capsular bag may vary from patient to patient so that it is desirable to have a lens suitable for different size capsular bags.

Moreover, the absence of a spring action may require too great a radial compressive force to deform the lens for implantation purposes as the surgeon introduces it through a small incision, with stress during and after implantation resulting. Consequently, it is desirable to have a lens that can be deformed slightly, radially as well as along the direction of the optical axis for this purpose.

SUMMARY OF THE INVENTION

This invention solves the problems outlined above with a circular lens having two resiliently deformable fixation members configured in a circular configuration that contacts most of the capsular equator in a manner similar to existing designs. Unlike existing designs, however, the fixation members are arranged so that they can be independently deformed in an advantageous manner. As a result, they flex slightly to overcome the above-mentioned problems.

So configured, the lens can better accommodate contraction of the capsular bag. It can better accommodate noncircular bags. It can be used for different size bags, and it can be deformed slightly for greater ease of implantation and reduction of stress.

Generally, an intraocular lens (IOL) constructed according to the invention includes an optic for implantation in a human eye and first and second fixation members attached to the optic for supporting the optic from the capsular bag of the eye. The fixation members may either be integrally attached or in the form of separate components that are attached by conventional means such as staking, each of the fixation members having inner and outer legs.

According to a major aspect of the invention, the inner leg of each of the fixation members extends radially outwardly and circumferentially from a respective one of first and second attachment sites on the optic to an intermediate portion of the fixation member. In addition, the outer leg of each of the fixation members extends along a respective one of first and second arcs from the intermediate portion of the fixation member to a distal end portion of the fixation member.

The first and second arcs extend along a circle that is centered on an optical axis of the optic, the circle has a diameter that is approximately equal to the diameter of the capsular bag, and each of the outer legs has a length such that the distal end portion of each of the fixation members is disposed proximate the intermediate portion of the other fixation member. As a result, the first and second fixation members can abut a substantial portion of the capsular equator of the capsular bag and yet flex radially inwardly more evenly than existing designs to accommodate variations in the diameter of the capsular equator while maintaining lens position.

In one embodiment of the invention, the first and second attachment sites are at generally diametrically opposite locations on the optic, the intermediate portions are at generally diametrically opposite locations on the circle, and each of the inner legs extends from a respective one of the attachment sites to a respective one of the intermediate portions along a spiralled path that encircles the optical axis for substantially more than ninety degrees to provide more uniform flexure characteristics.

According to another aspect of the invention, the first and second attachment sites lie in a radial plane of the optic and each of the inner legs is inclined to the radial plane. This results in the outer legs lying in a plane generally parallel to and spaced apart from the radial plane.

The above mentioned and other objects and features of this invention and the manner of attaining them will become apparent, and the invention itself will be best understood, by reference to the following description taken in conjunction with the accompanying illustrative drawings.

BRIEF DESCRIPTION OF THE DRAWINGS

FIG. 1 of the drawings is a perspective view of an intraocular lens constructed according to the invention;

FIG. 2 is a plan view of the lens;

FIG. 3 is a cross sectional view of the lens taken on line 3—3 of FIG. 2;

FIG. 4 is a plan view of a second lens embodiment employing three-piece construction;

FIG. 5 is a side view of a third lens embodiment in which the fixation members are inclined to a radial plane through the optic; and FIG. 6 is a side view of a fourth lens embodiment in which the inner legs are stepped.

DESCRIPTION OF THE PREFERRED EMBODIMENTS

Referring now to FIGS. 1-3, there is shown a lens 10 constructed according to the invention. Generally, the lens 10 includes an optic 11 and first and second fixation members 12 and 13 that are integrally attached to the optic 11 in a one-piece design fabricated according to known techniques from a PMMA material. The optic 11 is shaped to have desired optical characteristics and the first and second fixation members 12 and 13 are provided as means for supporting the optic 11 from the capsular bag of a human eye.

The first fixation member 12 has an inner leg 14 and an outer leg 15. Similarly, the second fixation member 13 has an inner leg 16 and an outer leg 17. These are arranged with the outer legs 15 and 17 extending along a substantial portion of a circle 18 that is centered on an optical axis 19 of the optic 11. In other words, the outer legs 15 and 17 extend along first and second arcs that are concave toward the optic. This results in better flexure characteristics while still enabling the fixation members 12 and 13 to abut most of the capsular equator.

The inner leg 14 of the first fixation member 12 extends radially outwardly and circumferentially from a first attachment site 20 on the optic 11 to an intermediate portion 21 of the first fixation member 12 that is located on the circle 18. Similarly, the inner leg 16 of the second fixation member 13 extends radially outwardly and circumferentially from a second attachment site 22 on the optic 11 to an intermediate portion 23 of the second fixation member 13 that is also located on the circle 18. As clearly shown in the drawings, each of the inner legs 14 and 16 is concave toward the optic and it extends circumferentially for a substantially greater distance than it extends radially, while each of the intermediate portions is substantially wider than the inner and outer legs 14-17.

The outer leg 15 of the first fixation member 12 extends along a first arc of the circle 18 from the intermediate portion 21 of the first fixation member 12 to a distal end portion 24 of the first fixation member 21, while the outer leg 17 of the second fixation member 13 extends along a second arc of the circle 18 from the intermediate portion 23 of the second fixation member 13 to a distal end portion 25 of the second fixation member 13. In other words, the outer legs 15 and 17 extend along first and second arcs that are concave toward the optic.

In the lens 10, the attachment sites 20 and 22 are at approximately diametrically opposite locations on the optic 11 and the intermediate portions 21 and 23 are also at approximately diametrically opposite locations on the circle 18. Configured in this manner, the first and second fixation members 12 and 13 are disposed symmetrically about a point 26 located along the optical axis 19. This results in a more even force distribution. In addition, the inner legs 14 and 16 extend along spiralled paths in the illustrated lens 10 that extend substantially more than ninety degrees. This also improves the force distribution.

In other words, the flexure of one of the fixation members 12 and 13 resulting from a force directed radially inwardly against its outer leg is relatively uniform irrespective of where on the outer leg the force is applied.

In addition, the outer legs 15 and 17 are sufficiently long so that the distal end portion 24 is proximate the intermediate portion 23 and the distal end portion 25 is proximate the intermediate portion 21. They are proximate in the sense that they are sufficiently spaced apart to enable flexure without the distal end portions abutting the intermediate portions while not be spaced apart to the point of defeating the purpose of contact a substantial portion of the capsular equator. The illustrated outer legs 15 and 17 extend over at least 320 degrees of the circle 18 for this purpose, but this may vary somewhat and still be proximate for the purposes of the inventive concepts disclosed.

The circle 18 has a diameter generally equal to the diameter of the capsular equator (the inner diameter of the capsular bag in which the fixation members 12 and 13 of the lens 10 are to be placed. In other words, the outer legs are dimensioned and arranged to be received in the capsular bag. As an idea of size, the circle 18 of the lens 10 is about 9.0 mm to 11.5 mm in overall diameter, with the optic 11 being about 5.5 mm to 7.0 mm in diameter. Of course, these dimensions may vary within the broader inventive concepts disclosed according to the particular application and the size of the capsular bag.

Considering now FIG. 4, there is shown a second embodiment or lens 100 constructed according to the invention that is similar in many respects to the lens 10. For convenience many features are designated with reference numerals increased by one hundred over those designating similar features of the lens 10.

Unlike the lens 10, the lens 100 employs three-piece construction. Each of the inner legs 114 and 116 of the first and second fixation members 112 and 113 are separately attached to the optic 111 by conventional means, such as by staking. This is done at the attachment sites A and B as illustrated by the dashed lines extending into the optic 11. Thus, one-piece construction is not the only alternative.

FIG. 5 illustrates a third embodiment or lens 200 that is generally similar to the lens 10 except that the inner legs 214 and 216 are inclined so that the outer legs 215 and 217 are generally parallel and spaced apart from a radial plane 201 through the optic 211 in which the attachment sites lie. Only the attachment site 220 is visible in FIG. 5, corresponding to the attachment site 22 in FIG. 1, a second attachment site corresponding to the attachment site 22 in FIG. 1 lying on the other side of the optic 211.

FIG. 6 illustrates a fourth embodiment or lens 300 that is generally similar to the lens 200 except that the inner legs 314 and 316 bend away from the radial plane 301. A bend 302 in the inner leg 314 combines with a similar bend in the inner leg 316 (not visible in FIG. 6) to do this.

The offset arrangement illustrated in FIGS. 5 and 6 is used to minimize vault under compression in the capsular bag. Consequently, it helps to facilitate rotation of the optic as forces compress on the haptics.

Thus, the intraocular lens of this invention overcomes various problems of the prior art. The fixation members are arranged so that they can be independently deformed in an advantageous manner. As a result, they flex slightly. The lens can better accommodate contraction of the capsular bag. It can better accommodate noncircular bags. It can be used for different size bags, and it can be deformed slightly for greater ease of implantation and reduction of stress.

Although an exemplary embodiment of the invention has been shown and described, many changes, modifications, and substitutions may be made by one having ordinary skill in the art without necessarily departing from the spirit and scope of the invention.

What is claimed is:

1. An intraocular lens, comprising:

an optic for implantation in a human eye; and first and second fixation members attached to the optic for supporting the optic in the eye, each of the fixation members having inner and outer legs;

the inner leg of each of the fixation members extending radially outwardly and circumferentially in a first circumferential direction from a respective one of first and second attachment sites on the optic to an intermediate portion of the fixation member, each of said inner legs being concave toward the optic;

the outer leg of each of the fixation members extending in a second circumferential direction along a respective one of first and second arcs from the intermediate portion of the fixation member to a distal end portion of the fixation member, which second circumferential direction is opposite to the first circumferential direction;

the first and second arcs being concave toward the optic; and each of the outer legs having a length such that the distal end portion of each of the fixation members is disposed proximate the intermediate portion of the other fixation member.

2. An intraocular lens as recited in claim 1, wherein: said inner legs extend along spiralled paths.

3. An intraocular lens as recited in claim 1, wherein: the intermediate portion of each fixation member is substantially wider than the inner and outer legs of the fixation member.

4. An intraocular lens, comprising:

an optic for implantation in a human eye; and first and second fixation members attached to the optic for supporting the optic in the eye, each of the fixation members having inner and outer legs;

the inner leg of each of the fixation members extending radially outwardly and circumferentially in a first circumferential direction from a respective one of first and second attachment sites on the optic to an intermediate portion of the fixation member, said intermediate portion being substantially wider than said inner and outer legs;

the outer leg of each of the fixation members extending in a second circumferential direction along a respective one of first and second arcs from the intermediate portion of the fixation member to a distal end portion of the fixation member, which second circumferential direction is opposite to the first circumferential direction; and the first and second arcs being concave toward the optic;

each of the outer legs having a length such that the distal end portion of each of the fixation members is disposed proximate the intermediate portion of the other fixation member.

* * * * *